United States Patent [19]

Hector et al.

[11] Patent Number: 5,616,321

[45] Date of Patent: Apr. 1, 1997

[54] METHOD OF TREATING BACTERIAL MENINGITIS WITH ANTI-TUMOR NECROSIS FACTOR ANTIBODY

[75] Inventors: Richard F. Hector, Dublin, Calif.; Michael S. Collins, Madison, Conn.

[73] Assignee: Bayer Corporation, Berkeley, Calif.

[21] Appl. No.: 410,006

[22] Filed: Mar. 23, 1995

Related U.S. Application Data

[63] Continuation of Ser. No. 246,929, May 20, 1994, abandoned, which is a continuation of Ser. No. 937,939, Aug. 28, 1992, abandoned.

[51] Int. Cl.$^6$ ............ A61K 39/395; A61K 49/00; C07K 16/24; C07K 16/28
[52] U.S. Cl. ............ 424/145.1; 424/150.1; 424/141.1; 424/156.1; 424/164.1; 530/388.23; 530/388.2; 530/388.4; 530/388.85
[58] Field of Search ............ 424/150.1, 141.1, 424/145.1; 530/388.4, 388.1, 388.23, 388.2, 388.85; 435/240.27

[56] References Cited

U.S. PATENT DOCUMENTS

| | | | |
|---|---|---|---|
| 5,075,236 | 12/1991 | Yone et al. | 436/518 |
| 5,231,024 | 7/1993 | Moeller et al. | 435/240 |
| 5,360,716 | 11/1994 | Ohmoto et al. | 435/7.2 |
| 5,436,154 | 7/1995 | Barbanti et al. | 435/240 |

FOREIGN PATENT DOCUMENTS

| | | |
|---|---|---|
| 0387095A1 | 12/1990 | European Pat. Off. . |
| 0186833B1 | 8/1992 | European Pat. Off. . |
| 0334165B1 | 12/1995 | European Pat. Off. . |
| 91/04054 | 4/1991 | WIPO . |
| 92/03145 | 3/1992 | WIPO . |
| 92/16553 | 10/1992 | WIPO . |
| 94/08619 | 4/1994 | WIPO . |
| 94/13322 | 6/1994 | WIPO . |
| 95/15179 | 6/1995 | WIPO . |

OTHER PUBLICATIONS

Craig, C., BioWorld Today, 5 (138):pp. 1 and 3, Jul. 19, 1994.
Pennington, J., Asm News, 58(9):479–482, Sep.1992.
Rhein, R., Biotechnology Newswatch, pp. 1 and 3, Oct. 4, 1993.
Roos, K.L., Clinical Neurpharmacology, 18(2): 138–147, 1995.
Ramito, O. et al., J. Exp. Med., 172:497–507, Aug. 1990.
Gess, A.S. et al., I & I, 61(7):2741–2747, Jul. 1993.
Tuomanen, E. I., J. Exp Med., 170:959–968, Sep. 1989.
Tracey, K.J., et al, Nature, 330:662–664, Dec. 1987.
Peltola, H. et al., Lancet, pp. 1281–1287, Jun. 10, 1989.
Williams, A.E., "Relationship Between Intracellular Survival in Macrophages and Pathogenicity of *Streptococcus suis* Type 1 Isolates", Microbial Pathogenesis, 8: 189–196 (1990).

Mogollon, J.D., et al., "Characterization of Prototype and Clinically Defined Strains of *Streptococcus suis* by Genomic Fingerprinting", J. Clinical Microbiol., vol. 28, No.11, pp. 2462–2466 (Nov. 1990).
Dupas, D., et al., "*Streptococcus suis* Meningitis: A Severe Noncompensated Occupational Disease", J. Occupational Medicine, vol. 34, No. 11, pp. 1102–1105 (Nov. 1992).
Arditi et al., "Cerebrospinal Fluid Cachectin/Tumor Necrosis Factor-$\alpha$ and Platelet–Activating Factor Concentrations and Severity of Bacterial Meningitis in Children", *Journal of Infectious Diseases*, vol. 162:139–147 (1990).
Arditi et al., "Cerebrospinal Fluid Endotoxin Levels in Children with *H. influenzae* Meningitis before and after Administration of Intravenous Ceftriazone", *Journal of Infectious Diseases*, vol. 160:1005–1011 (1989).
Beutler, Milsark, and Cerami, "Passive Immunization Against Cachectin/Tumor Necrosis Factor Protects Mice from Lethal Effect of Endotoxin" *Science*, vol. 229:869–871 (1985).
Swartz, "Bacterial Meningitis", in Wyngaarden, et al., eds., *Textbook of Medicine*, 19th ed., W.B. Saunders Co., Philadelphia, pp.:1655–1661.
Hinshaw et al., "Survival of Primates in $LD_{100}$ Septic Shock Following Therapy with Antibody to Tumor Necrosis Factor ($TNF_\alpha$)", *Circ. Shock*, vol. 30:279–292 (1990).
Mathison et al., "Participation of Tumor Necrosis Factor in the Mediation of Gram Negative Bacterial Lipopolysaccharide–induced Injury in Rabbits", *J. Clin. Invest.*, vol. 81:1925–1937 (1988).
Mustafa et al., "Modulation of Inflammation and Cachectin Activity in Relation to Treatment of Experimental *Hemophilus influenzae* Type b Meningitis", *J. Infect. Dis.*, vol. 160,No. 5:818–825 (1989).
Mustafa et al., "Cerebrospinal Fluid Prostaglandins, Interleukin 1$\beta$, and Tumor Necrosis Factor in Bacterial Meningitis", *Am. J. Dis. Children*, vol. 144:883–887 (1990).
Saukkonen et al., "The Role of Cytokines in the Generation of Inflammation and Tissue Damage in Experimental Gram–Positive Meningitis", *J. Exper. Med.*, vol. 171:439–448 (1990).
Tauber and Sande, "Pharmacodynamics of Antibiotics of Experimental Bacterial Meningitis–Two Sides of Rapid Bacterial Killing in the Cerebrospinal Fluid", *Scand. J. Infect. Dis. Supp.*, 74:173–179 (1991).
Tracey J.K. et al., "Anti–cachectin/TNF monoclonal antibodies prevent septic shock during lethal bacteraemia", *Nature*, vol. 330:662–664 (1987).

*Primary Examiner*—Susan A. Loring
*Attorney, Agent, or Firm*—James A. Giblin; Elizabeth F. Enayati; Alexandra J. Baran

[57] ABSTRACT

Bacterial meningitis infection in a mammal is treated by intravenous infusion of a therapeutically effective amount of a monoclonal antibody which binds to tumor necrosis factor alpha and an antibiotic. Treatment can be initiated up to five hours after bacterial challenge and the antibiotic is preferably selected from cephalosporins and aminoglycosides.

14 Claims, No Drawings

METHOD OF TREATING BACTERIAL MENINGITIS WITH ANTI-TUMOR NECROSIS FACTOR ANTIBODY

CROSS REFERENCE TO RELATED APPLICATIONS

This is a continuation of application Ser. No. 08/246,929, filed May 20, 1994, now abandoned, which is a continuation of application Ser. No. 07/937,939 filed Aug. 28, 1992, now abandoned.

FIELD

This application is concerned generally with a treatment of infection and specifically with the use of monoclonal antibodies that bind to TNF to treat bacterial meningitis.

PRIOR ART

Bacterial meningitis remains one of the more difficult management problems in clinical medicine. Evidence suggests that bacterial meningitis represents infection in a site with a reduced potential for host resistance. With essentially no antibodies or complement present in the spinal fluid, polymorphonucleocytes are essentially unable to contribute to the clearing of the intruding bacteria in the early steps of disease. Morbidity and mortality from bacterial meningitis remains high; a death rate of 30% for pneumococcal meningitis has not changed over the past 40 years despite new antibiotics and improved understanding of therapy practices. Bacterial meningitis is described in detail in Cecil, Textbook of Medicine, 19th addition at pages 1655–161, the details of which are incorporated into this application.

The role of tumor necrosis factor (TNF) in bacterial meningitis is described in an article by Arditi et al. in the Journal of Infectious Diseases, 162:p. 139–145(1990). See also related articles by Arditi et al., in the Journal of Infectious Diseases, vol. 160, no. 6, pp. 1005–1011, December 1989 and an article by Mustafa et al., the Journal of Infectious Diseases, vol. 160, no. 5, pp. 818–825, November 1989.

Recently, the role of cytokines in gram positive meningitis was described in an article by Saukkonen et al., the Journal of Experimental Medicine, Vol. 171, pp. 439–448, February 1990. In the above-cited article, polyclonal serum having antibodies that bind to TNF was delivered directly to the brain simultaneously with the microorganism initiating the meningitis.

Although current practices include rapid diagnostic procedures and aggressive treatment with the latest third-generation cephalosporins (among others), many patients fall victim to the disease despite the prompt sterilization of the cerebrospinal fluid. This unexpected outcome may result from harmful interactions between host cells and tissues and bacterial components released by treatment with lytic antibiotics (Scand. J. Infect., Dis. Supp. 74:173–179,1991). The burst of peptidoglycan, capsular polysaccharide and lipopolysaccharide liberated from the bacteria induce the production of a number of mediators including TNF in the central nervous system leading to meningeal and perivascular inflammation in the subarachnoid space. Disruption of the blood brain barrier ensues, leading to cerebral edema, ischemia, and a dramatic increase in intracranial pressure. Those that survive the acute phase of disease are often left with multiple neurological sequelae.

The lack of success with present clinical practices to reduce morbidity and mortality among victims of bacterial meningitis has led some investigators to experiment with procedures to reduce inflammation. Previous results from trials utilizing steroid-based anti-inflammatories either prior to or concomitant with antibiotic administration suggest that such an approach may have value. Mustafa et al., American Journal of Diseases of Children, Vol. 144, pp. 883–887, August 1990.

In other forms of life-threatening bacterial infections, most notably sepsis, the prevention of inflammation has been associated with a favorable outcome. Specifically, intervention with the production and activity of the proinflammatory-cytokine tumor necrosis factor has received considerable attention.

Treatment of experimentally-induced sepsis with antibiotics and antibodies capable of neutralizing tumor necrosis factor was found to result in a higher rate of survival in comparison to animals treated with antibiotics alone. However, for efficacy to be demonstrated in sepsis, it was necessary to infuse antibody to TNF within 30 min of bacterial or endotoxin challenge. See Mathison et al., Journal of Clinical Investigation, Vol. 81, pp. 1925–1937, June 1988, and also Hinshaw et al., Circulatory Shock, Vol 30, pp. 279–292, 1990.

Given the intravenous route of administration of this protein-based therapeutic, the likelihood of its usefulness in meningitis seemed small. This conclusion was based on the assumption of poor penetration of this macromolecule across the blood-brain barrier and restrictive timing of administration of the anti-tumor necrosis factor for the prevention of death due to sepsis under experimental conditions.

Indeed, the prior art teaches that administration of sufficient quantities of neutralizing antibodies to TNF must be done either prior to (Butler, Milsark, and Cerami, Science 229:869–871, 1985; Tracey et al., Nature 330:662–664, 1987) or concomitant with (Linshaw et al., Circ. Shock 30:279–292, 1990; Saukkonen et al., J. Exp. Med. 171:439–448, 1990) the endotoxin or bacterial challenge. Unlike the prior art, we found, quite surprisingly, that delay of treatment of up to five hours with anti-TNF monoclonal antibodies resulted in statistically significantly increased survival.

The present application describes the unexpected findings that intravenous administration of a monoclonal antibody preparation to tumor necrosis factor several hours after initiation of fulminate bacterial meningitis augments the activity of antibiotics and leads to enhanced survival and improved clinical status of animals in comparison to animals treated with antibiotics alone.

SUMMARY OF THE INVENTION

We have found that intravenous infusion of monoclonal antibodies to TNF are effective in treating a mammal having an infection of bacterial meningitis. Our method is effective up to at least five hours after infection and especially useful for the treatment of gram negative infections by augmentation of traditional anti-bacterial chemotherapy using antibiotics such as cephalosporins or aminoglycosides.

Our method involves intravenous infusion of monoclonal antibodies that bind to TNF (anti-TNF) in an amount sufficient to treat a meningitis infection in a mammal. In another embodiment a monoclonal anti-TNF is sufficient to neutralize the TNF produced by the mammal in response to the meningitis. It is thought that the treatment described herein is especially useful against *Escherichia coli* meningitis.

As used herein the term therapeutically effective amount (of monoclonal anti-TNF) means an amount, expressed as mg/kg body weight, sufficient to result in clinical improvement in the signs and symptoms of disease and/or prevention of mortality in the more critically ill mammal. That effective amount (or dose) ranges from about 1 mg/kg to 20 mg/kg mammal body weight, preferably about 15 mg/kg.

Pharmaceutically acceptable vehicle means a carrier suitable for delivery of safe and efficacious amounts of anti-TNF by the intravenous route.

Intravenously means injection directly into the blood circulatory system as done, for example, via venous or arterial routes (and as distinct from intracranial or spinal administration).

SPECIFIC EMBODIMENTS

The Anti-TNF Preparation: In the examples below, the monoclonal antibody preparation was a murine anti human TNF immunoglobulin G known as A10G10 expressed from a hybridoma cell line deposited with American Type Culture Collection (ATCC), 12301 Parklawn Drive, Rockville, Md. 20852, the cell line being deposited on 8 Jun. 1988 and having Accession No. HB 9736. The deposited cell line will be maintained in accordance with the Budapest Treaty. All restrictions on the availability to the public of the deposited cell line will irrevocably be removed upon the granting of a patent.

Strains and conditions of culture

*Escherichia coli* strain 050:K1 was employed in illustrative studies. For the growth of bacteria, brain-heart infusion broth was inoculated from frozen stock cultures and allowed to grow two hours at 37° C. The bacteria were collected by centrifugation, the pellet was washed and resuspended to the desired concentration.

In vivo studies

A pig mammalian model of meningitis was used to assess the monoclonal anti-TNF in vivo. Outbred Chester-White pigs, weighing 8–11 kg., were anesthetized, then infected intracisternally with either $6\times10^5$ cfu (for physiological assessment) or $2\times10^7$ cfu (for survival studies). For physiological studies, a total of eight pigs was infected, then divided into two groups of four each for testing. For survival studies, a total of 26 pigs were infected and divided into two groups of 13 each for testing.

For physiological studies, three hours after infection pigs were again anesthetized. One group was given 15 mg/kg of the monoclonal anti-TNF via intravenous infusion in an ear vein, while the other group was given placebo (consisting of the pharmaceutical vehicle). Also, all animals were given 5 mg/kg of gentamicin sulfate intramuscularly three hours after infection. Six hours after infection (and three hours after treatment) the pigs were again anesthetized and blood and cerebral spinal fluid was removed for study.

For survival studies, five hours after infection pigs were anesthetized. One group was given 15 mg/kg of the monoclonal anti-TNF via intravenous infusion in an ear vein, while the other group was given placebo (consisting of the pharmaceutical vehicle). All animals were given 75 mg/kg of ceftriaxone intramuscularly. Surviving animals were given subsequent 50 mg/kg doses of ceftriaxone 24 and 48 hours after infection. Animals in this experiment were observed for mortalities for seven days.

Results:

Physiological studies

Cerebral spinal fluid from the animals was assessed for presence of tumor necrosis factor (TNF), interleuken 6 (IL-6), lactate, glucose, white blood cells, and bacteria. Both blood and spinal fluid were assessed for the concentration of anti-TNF to determine the degree of penetration of the immunoglobulin across the blood-brain barrier into the central nervous system. Results from the spinal fluid demonstrated that in pigs treated with the monoclonal anti-TNF, no detectable TNF was present. In contrast, pigs treated only with antibiotics had an average of 42 picograms per ml of TNF. Also, the spinal fluid from anti-TNF treated pigs had reduced levels (at least 77% reduction) of the cytokine IL-6, with an average of 2,747 units per ml, in comparison to control animals with an average of 12,087 units per ml.

Animals treated with the anti-TNF monoclonal antibodies did not have discernible differences in pleocytosis, lactate, glucose, or reduced numbers of bacteria in comparison to controls. These results are summarized in Table I below.

TABLE I

| GROUP | RESULTS OF SPINAL FLUID DETERMINATIONS ||||||
|---|---|---|---|---|---|---|
| | TNF pg/ml | IL-6 units/ml | LACTATE mg/100 ml | GLUCOSE mg/100 ml | WBC × 10e6/ml | BACTERIA CFU/ml |
| Control | 41.5 ± 8.5 | 12,087 | 5.0 ± .2 | 83 ± 11 | 4.00 ± 2 | 5.62 × 10e4 |
| Anti-TNF | <5 | 2,747 | 4.3 ± .1 | 95 ± 2 | 5.07 ± .09 | 3.18 × 10e5 |

The average penetration of the monoclonal anti-TNF into the cerebral spinal fluid was determined to be 4.5% of serum values.

Survival Studies:

Deaths in the control group, treated with ceftriaxone only, had rapid onset, reaching 77% 24 hours after infection. In contrast, in pigs treated with the monoclonal anti-TNF and ceftriaxone, deaths accounted for only 15% of the total 24 hours after infection. By the end of the experiment, seven days after infection, 92% of control animals had died while only 38% of the monoclonal anti-TNF group had died. The results are summarized in the Table II below.

TABLE II

| TREATMENT GROUP | SURVIVAL RESULTS DEAD/TOTAL AT INTERVAL | | |
|---|---|---|---|
| | 24 h | 48 h | 7 days |
| Control | 10/13 | 10/13 | 12/13 |
| Anti-TNF | 2/13 | 4/13 | 5/13 |

Discussion

The data indicate that monoclonal anti-TNF, when used in conjunction with antibiotics, can serve as an efficacious agent in established bacterial meningitis infections. In a surprising finding, the physiologic study indicated that the intravenous administration of monoclonal anti-TNF in animals infected with *Escherichia coli* in the central nervous system can lead to the neutralization of TNF in the cerebral spinal fluid, and results in the reduced production of the cytokine IL-6.

In the survival experiments, the results indicated that animals (mammals) infected with a potentially lethal challenge of *Escherichia coli* in the central nervous system can be protected by intravenously-administered monoclonal anti-TNF in combination with an antibiotic, and that this protection is evident for a period of at least seven days after infection. Therefore, it is thought that this agent should be considered as a therapeutic agent in human use for the described bacterial meningitis as well as for other medically important bacteria capable of causing this disease.

Given the active disclosure it is thought that variations of treatment will occur to those skilled in treatment of infectious diseases. Accordingly, it is intended that the above examples should be construed as illustrative and the invention disclosed here should be limited only by the following claims.

We claim:

1. A method of treating a bacterial meningitis infection in a mammal comprising intravenously administering to the mammal a therapeutically effective amount of a monoclonal antibody which binds to tumor necrosis factor, wherein said antibody is administered up to five hours after onset of the infection and being in addition to the administration of an antibiotic.

2. The method of claim 1 wherein the antibiotic is selected from the group consisting of cephalosporins and aminoglycosides.

3. The method of claim 1 wherein the antibodies is included in a pharmaceutically acceptable vehicle.

4. The method of claim 3 wherein the amount of antibody ranges from about 1 to 20 mg/kg of mammal body weight.

5. The method of claim 1 wherein the antibiotic is selected from ceftriaxone and gentamicin.

6. The method of claim 1 wherein the administration is under conditions to allow at least 0.5% of the serum antibody to penetrate the blood-brain barrier of the mammal.

7. The method of claim 1 wherein the administration is under conditions sufficient to result in a significant reduction of IL-6 in spinal fluid of the mammal.

8. The method of claim 7 wherein the IL-6 reduction is at least 50%.

9. A method of treating a bacterial meningitis infection in a mammal comprising intravenously administering to the mammal a therapeutically effective amount of a monoclonal antibody produced by a hybridoma having an ATCC Accession No. HB 9736, wherein said antibody is administered up to five hours after onset of the infection and being in addition to the administration of an antibiotic.

10. The method of claim 9 wherein the antibiotic is selected from the group consisting of cephalosporins and aminoglycosides.

11. The method of claim 9 wherein the antibiotic is ceftriaxone.

12. The method of claim 9 wherein the meningitis infection is caused by a gram negative bacterium.

13. The method of claim 12 wherein the bacterium is *Escherichia coli*.

14. A method of treating a bacterial meningitis infection in a mammal comprising intravenously administering to the already infected mammal a therapeutically effective amount of a monoclonal antibody produced by a hybridoma having an ATCC Accession No. HB 9736, wherein said antibody is administered up to five hours after onset of the infection and being in addition to the administration of an antibiotic.

* * * * *